United States Patent [19]
Kyle et al.

[11] Patent Number: 5,686,565
[45] Date of Patent: Nov. 11, 1997

[54] BRADYKININ ANTAGONIST PSEUDOPEPTIDE DERIVATIVES OF AMINOALKANOIC ACIDS AND RELATED OLEFINS

[75] Inventors: Donald James Kyle, Abingdon; Babu Joseph Mavunkel, Timonium, both of Md.

[73] Assignee: Scios Inc., Mountain View, Calif.

[21] Appl. No.: 281,904

[22] Filed: Jul. 28, 1994

Related U.S. Application Data

[63] Continuation-in-part of Ser. No. 118,550, Sep. 9, 1993, Pat. No. 5,552,383, which is a continuation-in-part of Ser. No. 957,879, Oct. 8, 1992, Pat. No. 5,521,158.

[51] Int. Cl.$^6$ .................................................. A61K 38/08
[52] U.S. Cl. ............................... 530/328; 514/15; 514/16
[58] Field of Search .................... 514/15–17; 530/328, 530/329, 314

[56] References Cited

U.S. PATENT DOCUMENTS

| | | | |
|---|---|---|---|
| 4,242,329 | 12/1980 | Claeson et al. | 424/177 |
| 4,483,850 | 11/1984 | Patchett et al. | 424/177 |
| 4,693,993 | 9/1987 | Stewart et al. | 514/14 |
| 4,801,613 | 1/1989 | Stewart et al. | 514/14 |
| 4,822,984 | 4/1989 | Geiger et al. | 548/252 |
| 4,923,963 | 5/1990 | Stewart et al. | 530/314 |

FOREIGN PATENT DOCUMENTS

| | | |
|---|---|---|
| 0334685 | 9/1989 | European Pat. Off. |
| 0 370 453 | 5/1990 | European Pat. Off. |
| 0 413 277 | 2/1991 | European Pat. Off. |
| 92/18155 | 10/1992 | WIPO |
| 92/18156 | 10/1992 | WIPO |
| WO 94/08607 | 4/1994 | WIPO |

OTHER PUBLICATIONS

Karanewsky et al., "(Phosphinyloxy)acyl amino acids inhibitors of angiotensin converting enzyme. 2. Terminal amino acid analogues of (S)-1-[6-amino-2[[hydroxy(4-phenylbutyl)phosphinyl]oxy]-1-oxohexyl]-L-proline" *J. Med. Chem.* (1990) 33(5):1459–1469.

Smith et al., "Synthesis and pharmacological activity of angiotensin converting enzyme inhibitors: N-(mercaptoacyl)-4-substituted-(S)-prolines" *J. Med. Chem.* (1988) 31(4):875–885.

Krapcho et al., "Angiotensin converting enzyme inhibitors. Mercaptan, carboxyalkyl dipeptide, and phosphinic acid inhibitors incorporating 4-substituted prolines" *J. Med. Chem.* (1988) 31(6):1148–1160.

Hock et al., "Hoe 140 a new potent and long acting bradykinin antagonist: in vitro studies" *Br. J. Pharmacol.* (1991) 102:769–744.

Wirth et al., "Hoe 140 a new potent and long acting bradykinin antagonist: in vivo studies" *Br. J. Pharmacol.* (1991) 102:774–777.

Pongracic et al., "A competitive kinin receptor antagonist, [DArg$^0$, Hyp$^3$, DPhe$^7$]–bradykinin, does not affect the response to nasal provocation with bradykinin" *Br. J. Pharmacol.* (1991) 31:287–294.

Higgins et al., "A study of the efficacy of the bradykinin antagonist NPC567 in rhinovirus infections in human volunteers" *Chemical Abstracts* (1991) 114:220805d.

Soler et al., "A bradykinin antagonist amodifies ntigen–induced airway hyper–responsiveness and airway inflammation in allergic sheep" *Am. Rev. Respir. Dis.* (1989) A327.

Stewart, John M., "Hydroxyproline analogs of bradykinin" *J. Med. Chem.* (1974) 17(5):537–539.

Stewart, John M., "Chemistry and biologic activity of peptides related to bradykinin" *Handbook of Experimental Pharmacol.* (1979) vol. XXV Supp, Springer–Verlag Berlin Heidelberg NY.

Vavrek et al., "Smooth muscle selectivity in bradykinin analogs with multiple D–amino acid substitutions", Dept. of Biochem., University of Colorado School of Medicine, Denver, Colorado.

Rifo et al., "Bradykinin receptor antagonists used to characterize the heterogeneity of bradykinin–induced responses in rat vas deferens" *Eur. J. Pharmacol.* (1987) 142:305–312.

Zeitlin et al., "Mobilization of tissue kallikrein in inflammatory disease of the colon" Wolfson Labs. Gastrointestinal Unit, West General Hospital and Dept. of Clinical Surgery, Univ. of Edinburgh (1972) pp. 113–138.

Suzuki et al., "Synthesis of every kind of peptide fragments of bradykinin" *Chem. Pharm. Bull.* (1969) 17:1671–1678.

Dray et al. "Bradykinin and inflammatory pain" *TINS* (1993) 16(3):99–104.

Perkins et al., "Antinociceptive activity of the bradykinin B$_1$ and B$_2$ receptor antagonists, des–Arg$^9$, [Leu$^8$]–BK and HOE 140, in two models of persistent hyperalgesia in the rat" *Pain* (1993) 53:191–197.

Zabrocki et al., "Conformational Mimicry. 3. Synthesis and incorporation of 1,5–disubstituted tetrazole dipeptide analogues into peptides with preservation of chiral integrity: bradykinin" *J. Org. Chem.* (1992) 57(1):202–209.

Hodges et al. (eds.) *Peptides, Chemistry, Structure and Biology: Proceedings of the 13th American Peptide Symposium Jun. 20–25, 1993* (ESCOM: Leiden, 1994), pp. 381–383.

(List continued on next page.)

*Primary Examiner*—Robert J. Hill, Jr.
*Assistant Examiner*—David Lukton
*Attorney, Agent, or Firm*—Peter R. Shearer; Marjorie L. Jarvis

[57] ABSTRACT

Pseudopeptide compounds based on a modified bradykinin sequence are potent bradykinin receptor antagonist. All or a portion of the amino acids at positions 2 through 5 of the bradykinin sequence are replaced by 2-pyrrolidinyl and/or amino-alkanoic acid or related olefinic derivatives to reduce the peptidic nature of the compounds.

The analogs produced are useful in treating conditions and diseases of a mammal and human in which an excess of bradykinin or related kinins are produced or injected such as by insect bites.

2 Claims, No Drawings

OTHER PUBLICATIONS

Kyle et al., "A proposed model of bradykinin bound to the rat $B_2$ receptor and its utility for drug design" *J. Med. Chem.* (1994) 37(9):1347–1354.

*Abstracts of Papers, Part 1: 208th American Chemical Society National Meeting Aug. 21–25, 1994* 190.

Kyle et al., "NMR and computational evidence that high-affinity bradykinin receptor antagonists adopt C-terminal β-turns" *J. Med. Chem.* (1993) 36(10):1450–1460.

Hodges et al. (eds.) *Peptides, Chemistry, Structure and Biology: Proceedings of the 13th American Peptide Symposium Jun. 20–25, 1993* (ESCOM: Leiden, 1994), pp. 449–451.

BRADYKININ ANTAGONIST PSEUDOPEPTIDE DERIVATIVES OF AMINOALKANOIC ACIDS AND RELATED OLEFINS

This application is a continuation-in-part of U.S. application Ser. No. 08/118,550 filed Sep. 9, 1993, now U.S. Pat. No. 5,552,383 which is a continuation-in-part of U.S. application Ser. No. 07/957,879 filed Oct. 8, 1992, now U.S. Pat. No. 5,521,158.

FIELD OF THE INVENTION

This invention relates to compounds which are bradykinin receptor antagonism, pharmaceutical compositions and methods for using these compounds to antagonize the effects of bradykinin in mammals, including humans. The invention relates to pseudopeptides which are potent bradykinin receptor antagonists.

More particularly, the invention relates to the replacement of all or a portion of the amino acids Pro-Pro-Gly-Phe found at positions 2 through 5 of bradykinin with a substituted amino-alkanoic acid or related oleic derivative. The invention also relates to the substitution of 2-pyrrolidinyl for either of the prolines at positions 2 or 3. The pseudopeptide also includes additional modifications at other positions within the modified bradykinin molecule which confer increased antagonist potency, resistance to enzymatic degradation and/or tissue specificity.

BACKGROUND OF THE INVENTION

Bradykinin (BK) is a linear nonapeptide produced endogenously in humans and other mammals as a result of the activity of kallikreins, a group of proteolytic enzymes present in most tissues and body fluids, on kininogens. Once released, kinins produce many physiological responses, including pain and hyperalgesia by stimulating C- and A-fibers in the periphery. There is also considerable evidence that kinins contribute to the inflammatory response.

Native bradykinin has the amino acid structure shown in Table I:

TABLE I

| Arg—Pro—Pro—Gly—Phe—Ser—Pro—Phe—Arg |
| --- |
| 1    2    3    4    5    6    7    8    9 |

Bradykinin, and its physiologically important related peptides kalladin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its proinflammatory effects, bradykinin is a vasodilator. Because of its concomitant ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

As a result of the implication that increased levels of bradykinin may play a part in a number of pathological conditions, considerable research has been aimed toward the derivation of bradykinin receptor antagonists as potential therapeutic agents. A bradykinin receptor antagonist is expected to possess a number of desirable biological effects in the treatment, for example, of pain and inflammation, septic shock, airway disorders such as asthma, burn pain, pancreatitis, angioedema, certain nervous system disorders, chronic inflammation such as rheumatoid arthritis and inflammatory bowel disease, rhinitis, and allergy.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines, bradykinin-antibodies, benzodiazepine derivatives, high molecular weight ethylene oxide polymers, gallic acid esters, and serotonin inhibitors. None of these compounds or classes of compounds specifically inhibit the effects of bradykinin.

Heptyl esters of various amino acid-containing substances, such as single basic amino acids, the dipeptide Phe-Gly, and analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Several research groups have prepared bradykinin receptor antagonists. The first antagonists of bradykinin were discovered by Stewart and Vavrek. U.S. Pat. Nos. 4,801,613 and 4,693,993 (which references are incorporated in their entirety herein) disclose a series of bradykinin antagonists wherein the L-Pro at the 7-position of the peptide hormone bradykinin or other substituted analogs of bradykinin is replaced with an aromatic amino acid of the D-configuration which converts bradykinin agonists into bradykinin antagonists. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY. Typically, these bradykinin antagonist peptides had $K_i$ values in the range of 20–80 nM in guinea pig ileum (Stewart, J. M., et al., In Bradykinin Antagonists (1991) Burch, R. M., Marcel Dekker, New York).

Subsequently, several classes of bradykinin antagonist peptides with 600–1000-fold greater potency in the guinea pig ileum preparation have been disclosed. Published European Patent Application No. 0 413 277 A1 to Hoechst A. G. discloses bradykinin antagonists containing the aromatic amino acid D-Phe at position 7 but containing unnatural amino acids at position 8 which impart increased potency.

Published European Patent Application No. 0 370 453 A2 to Hoechst A. G. discloses bradykinin antagonists containing a D-imino acid (D-Tic) at position 7.

A more recent series of bradykinin receptor antagonist peptides lacks the D-aromatic amino acid at position 7 which was believed to be critical to the activity of the earlier described antagonists of the endogenous neuropeptide. As described in published PCT application WO 92/18156 and WO 92/18155 (which references are incorporated in their entirety herein) this group of compounds has a general bradykinin antagonist structure wherein the L-Pro at position 7 is substituted with hydroxyproline ether and thioether derivatives (termed D-Hype) and the L-Phe at position 8 can additionally be substituted with hydroxyproline ethers and thioethers derivatives (Hype), Tic or Oic.

The bradykinin antagonist peptides referred to above exert their activity by blocking the bradykinin $B_2$ receptor. A second bradykinin receptor, the $B_1$ receptor, is not expressed to any significant degree in healthy tissue, but its expression is upregulated during persistent inflammatory hyperalgesia. This receptor is activated by des $Arg^9$-Kalladin and des $Arg^9$-bradykinin, a proteolytic degradation product of bradykinin. It is belived to play an important role in the maintenance of hyperalgesia in chronic inflammatory conditions (Dray, A. and Perkins, M., TINS, Vol. 16, No. 3 (1993) 99–103). [Des-$Arg^9$] analogs of bradykinin $B_2$ receptor antagonist peptides of the type described above, bind to the $B_1$ receptor and have been shown to reverse or prevent hyperalgesia in animal models of persistent inflammatory hyperalgesia, whereas the corresponding $B_2$ receptor antagonism were ineffective or weakly active in these models (Perkins, M et al., Pain, 53, (1993) 191–197).

One limitation of the bradykinin antagonist peptides known to date is the necessity for parenteral administration. Due to the peptidic nature of the compounds, they are unlikely to be orally active. Further, peptides in general tend to have a relatively short duration of action as a consequence of their rapid metabolic degradation. As a result, non-peptide or pseudopeptide bradykinin receptor antagonists that lack the limitations of a peptide offer meaningful therapeutic advantages.

SUMMARY OF THE INVENTION

The present invention resides in the discovery that the novel pseudopeptide compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists.

More particularly, the invention relates to a modification of the sequence of the mammalian peptide hormone bradykinin and pharmaceutically acceptable salts thereof. The bradykinin modification contemplated by this invention includes the replacement of all or a portion of the amino acids Pro-Pro-Gly-Phe at position 2 through 5 with an alkanoic acid or related olefinic derivative, in addition to other modifications, to produce sequence-related analogs that act as specific and competitive inhibitors of the biological activities of bradykinin. The invention also relates to the substitution of 2-pyrrolidinyl for either the proline at position 2 or 3.

The invention relates more specifically to the formation of pseudopeptide compounds capable of competing with native sequence bradykinin for binding to the $B_2$ receptor having the formula:

A—B—C—D—E—F—G—H—I—J—K wherein

A is hydrogen or is selected from the group consisting of the L- and D-isomers of Arg, Gln, Ash, Lys, Sar, N-ε-acetyl-Lys, $N^G$-p-tosyl-Arg, $N^G$-nitro-Arg, Lys-Lys, acetyl-Arg, and citrulline;

B is a direct bond or is selected from the group consisting of the L- and D-isomers of Arg, Gln, Asn, Lys, Sar, N-ε-acetyl-Lys, $N^G$-p-tosyl-Arg, $N^G$-nitro-Arg, acetyl-Arg, and citrulline;

C is a direct bond or is selected from the group consisting of Pro, 4Hyp, Oic, dehydroPro, Tic, Aoc, L-azetidine-2-carboxylic acid, Eac, Gly, Thz and Aib;

D is selected from the group consisting of 2-pyrrolidinyl, Pro, 4Hyp, Oic, dehydroPro, Tic, Aoc, L-azetidine-2-carboxylic acid, Eac, Gly, Thz and Aib;

E has the following formula:

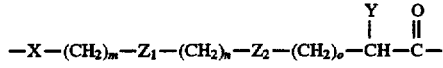

wherein

X is selected from the group consisting of a direct bond and an imino (—NH—) group;

$Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

Y is selected from the group consisting of hydrogen, hydroxymethyl, $C_1$ to $C_6$ alkyl, benzyl, thiophenylmethyl and furanylmethyl;

m, n, and o are independently 0 through 12, with the proviso that their total does not exceed 12

F is a direct bond or is an aromatic amino acid;

G is a direct bond or is selected from the group consisting of Ser, Thr, Gly, Val, Ala, Cys and Tyr;

H is selected from the group consisting of a D-aromatic amino acid and a D-Hype;

I is selected from the group consisting of Oic, Aoc, Thz, Tic, L-indoline-2-carboxylic acid, Aib, Leu, Ile, Val, Thi, octahydro-1H-isoindole-1-carboxylic acid, pipecolinic acid, Pro, 4Hyp, azetidine-2-carboxylic acid, Phe, and homoPhe, and a Hype;

J is selected from the group consisting of Arg, Orn, Asn, Gln, and Lys;

K is a hydroxyl group or a C-terminal extension selected from the group consisting of amide, alkoxy, and an acidic, basic, or neutral aliphatic, aromatic, or cyclic amino acid residue of the D- or L-configuration;

and pharmaceutically accepted salts thereof.

In another embodiment, the invention relates to pseudopeptide compounds capable of binding to the bradykinin $B_1$ receptor. These compounds, because of their ability of block $B_1$ receptor mediated hyperalgesia, are useful in the treatment of conditions associated with chronic intimation. In particular, these compounds have the same structure as that set forth above for the $B_2$ receptor antagonists with the exception that the amino acid residue representated by J is deleted.

Another embodiment of the invention involves a pharmaceutical composition useful as a bradykinin receptor antagonist comprising a pharmaceutical carrier and an effective amount of the novel bradykinin-type pseudopeptide. The invention also involves a process for antagonizing bradykinin receptor activity in mammals which comprises administering to a subject an effective amount of the novel compound to antagonize bradykinin receptor activity.

A further embodiment involves a pharmaceutical preparation for treating local pain and intimation from burns, wounds, cuts, rashes and other such trauma, and pathological conditions caused by the production of bradykinin or related kinins by an animal which comprises administering an effective amount of the novel pseudopeptide sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

The pseudopeptide compounds of the present invention are bradykinin receptor antagonists wherein an organic group exemplified by an alkanoic acid or related olefinic derivative substitutes and mimics the function of all or a portion of amino acids 2 through 5 (Pro-Pro-Gly-Phe) of native bradykinin. In addition, 2-pyrrolidinyl can substitute for either of the prolines at position 2 or 3. Any bradykinin-type molecule containing the disclosed 2-pyrrolidinyl and/or alkanoic acid derivative substitutes at positions 2 through 5 is contemplated by this invention.

A. Preferred Bradykinin-Type Peptide Structures

The preferred bradykinin-type peptides have the following formula:
Formula 1

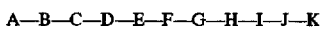

wherein

A is hydrogen or is selected from the group consisting of the L- and D-isomers of Arg, Gln, Asn, Lys, Sat, N-ε-acetyl-Lys, $N^G$-p-tosyl-Arg, $N^G$-nitro-Arg, Lys-Lys, acetyl-Arg, and citrulline;

B is a direct bond or is selected from the group consisting of the L- and D-isomers of Arg, Gln, Asn, Lys, Sar, N-ε-acetyl-Lys, $N^G$-p-tosyl-Arg, $N^G$-nitro-Arg, acetyl-Arg, and citrulline;

C is a direct bond or is selected from the group consisting of Pro, 4Hyp, Oic, dehydroPro, Tic, Aoc, L-azetidine-2-carboxylic acid, Eac, Gly, Thz and Aib;

D is selected from the group consisting of 2-pyrrolidinyl, Pro, 4Hyp, Oic, dehydroPro, Tic, Aoc, L-azetidine-2-carboxylic acid, Eac, Gly, Thz and Aib;

E has the following formula:

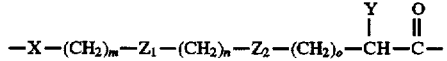

wherein

X is selected from the group consisting of a direct bond and an imino (—NH—) group;

$Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

Y is selected from the group consisting of hydrogen, hydroxymethyl, $C_1$ to $C_6$ alkyl, benzyl, thiophenylmethyl and furanylmethyl;

m, n, and o are independently 0 through 12, with the proviso that their total does not exceed 12

F is a direct bond or is an aromatic amino add;

G is a direct bond or is selected from the group consisting of Ser, Thr, Gly, Val, Ala, Cys and Tyr;

H is selected from the group consisting of a D-aromatic amino acid and a D-Hype;

I is selected from the group consisting of Oic, Aoc, Thz, Tic, L-indoline-2-carboxylic acid, Aib, Leu, Ile, Val, Thi, octahydro-1H-isoindole-1-carboxylic acid, pipecolinic acid, Pro, 4Hyp, azetidine-2-carboxylic acid, Phe, and homoPhe, and a Hype;

I is selected from the group consisting of Arg, Ore, Ash, Gln, and Lys;

K is a hydroxyl group or a C-terminal extension selected from the group consisting of amide, alkoxy, and an acidic, basic, or neutral aliphatic, aromatic, or cyclic amino acid residue of the D- or L-configuration;

and pharmaceutically accepted salts thereof.

Formula 2

Particularly preferred is a peptide wherein:

A is D-Arg;

B is Arg;

C is a direct bond or is selected from the group consisting of Pro, 4Hyp and Oic;

D is selected from the group consisting of 2-pyrrolidinyl, Pro, 4Hyp and Oic;

E has the following formula:

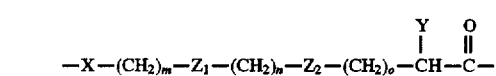

wherein

X is selected from the group consisting of a direct bond and an imino (—NH—) group;

$Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

Y is selected from the group consisting of hydrogen, hydroxymethyl, $C_1$ to $C_6$ alkyl, and benzyl;

m, n, and o are independently 0 through 12, with the proviso that their total does not exceed 16

F is a direct bond or is selected from the group consisting of Phe, Thi, n-benzyl Gly, Tyr, and Trp;

G is a direct bond or selected from the group consisting of Ser, Gly and Val;

H is selected from the group consisting of D-Phe, D-Tic and a D-Hype;

I is selected from the group consisting of Phe, Oic, Aoc, and a Hype;

J is Arg; and

K is selected from the group consisting of a hydroxyl group, an amide group and an alkoxy group.

Formula 3

If one wishes to produce a bradykinin antagonist which interacts with the $B_1$ receptor and is therefore useful for the treatment of chronic inflammatory conditions, then the pseudopeptide has the preferred formula

wherein A, B, C, D, E, F, G, H, and I are as described above for Formula 1. Particularly preferred $B_1$ receptor antagonists of this formula are those in which A, B, C, D, E, F, G, H, and I are as described above for Formula 2.

B. Preferred Aminoalkanoic Acids and Related Olefins

Preferred peptides include those wherein

C is a direct bond;

D is selected from the group consisting of 2-pyrrolidinyl and Oic;

E has the following formula:

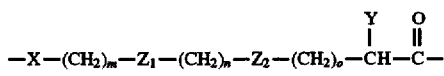

wherein

X is selected from the group consisting of a direct bond and an imino (—NH—) group;

$Z_1$ and $Z_2$ are independently selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

Y is selected from the group consisting of hydrogen, hydroxymethyl, $C_1$ to $C_6$ alkyl, benzyl, thiophenylmethyl and furanylmethyl;

m, n, and o are independently 0 through 12, with the proviso that their total does not exceed 12;

F is a direct bond;

G is a direct bond or Ser.

Preferably the aminoalkanoic acid or related olefins of E include those wherein $Z_1$ is selected from the group consisting of a direct bond, a $C_3$ to $C_8$ carbocycle, and a $C_2$ to $C_{18}$ monoolefin or a $C_4$ to $C_{18}$ polyolefin containing 1 to 5 double bonds which may optionally be incorporated into a cyclic system;

$Z_2$ is selected from the group consisting of a direct bond and a $C_2$ to $C_{18}$ monoolefin;

Y is selected from the group consisting of hydrogen and benzyl;

m, n, and o are independently 0 to 6.

Preferred cyclic systems incorporated into $Z_1$ or $Z_2$ include:

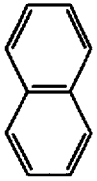

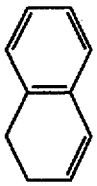

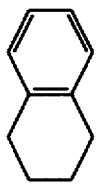

Other preferred embodiments include wherein E is selected from the group consisting of preferred cyclic systems incorporated into the $Z_1$ polyolefins include but are not limited to 4-amino-2-butenoyl;

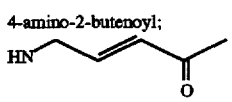

3-[2-(aminomethyl)phenyl]-2-propenoyl;

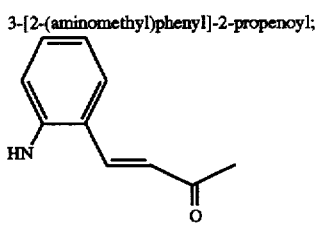

3-[2-(aminomethyl)phenyl]-2-propanoyl;

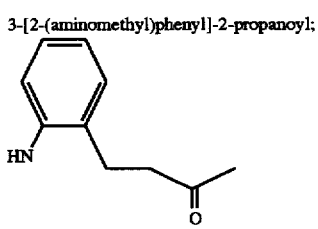

3-[3-(aminomethyl)phenyl]-2-propenoyl;

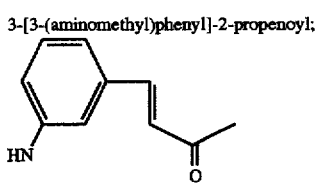

3-[3-(aminomethyl)phenyl]-2-propanoyl;

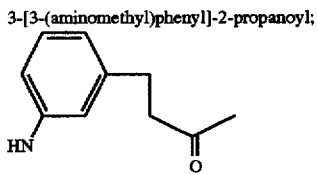

4-[2-(aminomethyl)phenyl]-3-butenoyl;

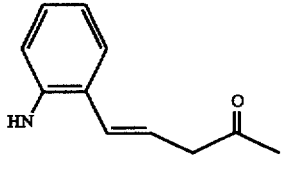

3-[2-(aminoethyl)phenyl]-2-propenoyl;

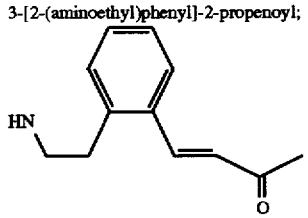

-continued
6-amino-4,5-(1,2-cyclohexyl)-2-hexenoyl;
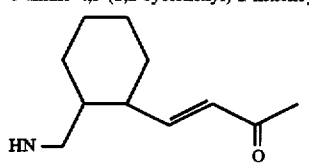
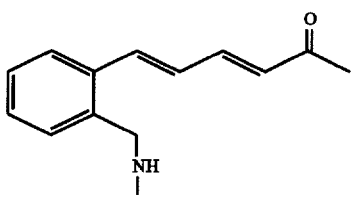
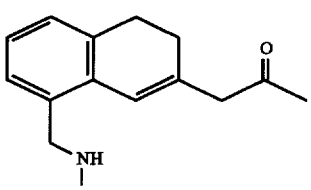
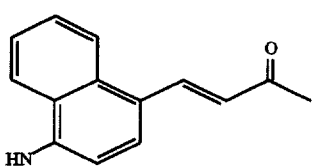
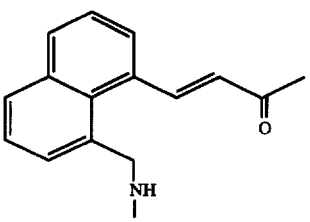
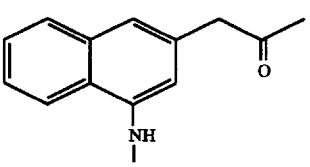
-continued
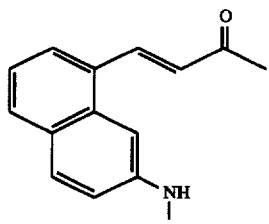
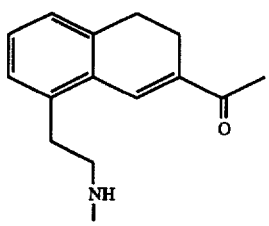
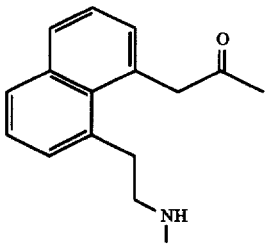
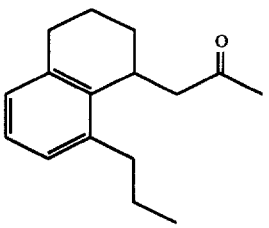
Particularly preferred are the following peptides:
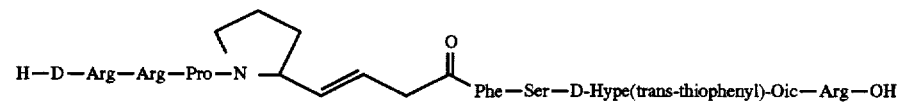
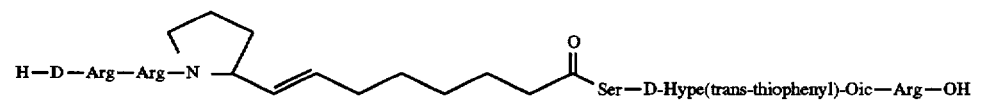

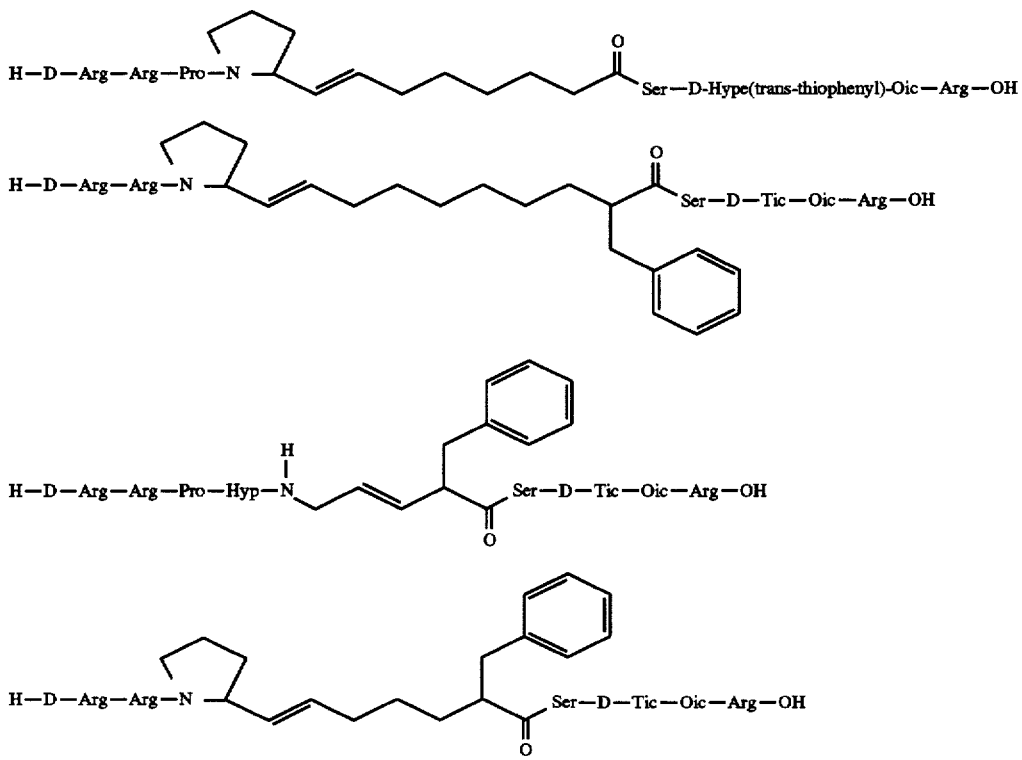

Specifically preferred $B_1$ receptor antagonists, for the treatment of chronic inflammatory conditions, are those in which the C-terminal arginine residue is deleted, i.e. the Oic residue is the C-terminal residue.

The following terms used herein in the specification and claims are further defined: "olefinic aminoalkenoyl" is a carbon chain of from 2 to 18 carbons containing at least one double bond, wherein 2 to 4 carbons may be optionally incorporated into a cyclic structure, having an amino acid linkage (i.e., an N-terminal amino group and a C-terminal carbonyl group). The alkenyl portion of the olefinic aminoalkenoyl is preferrably a hydrocarbon chain, but may also include carbon replacements, such as by nitrogen.

"2-pyrrolidinyl" is defined herein as having the following structure:

"Hype" is defined herein as having the following structure:

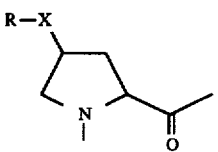

wherein R is selected from the group consisting of H, $C_1$–$C_6$ alkyl, substituted $C_1$–$C_6$ alkyl, $C_2$–$C_8$ alkenyl, $C_2$–$C_8$ cycloalkyl, $C_3$–$C_8$ cycloalkyl substituted $C_1$–$C_6$ alkyl, an aryl group, a substituted aryl group wherein the substituent is $C_1$–$C_4$ alkyl, $C_1$–$C_4$ alkoxy, halogen or trifluoromethyl, an arylalkyl group, and a group of the formula $R_1NHC(O)$- where $R_1$ is $C_1$–$C_6$ alkyl or aryl, and where X is either $SO_n$ or oxygen, and n=0, 1, or 2;

"cycloalkyl" is a saturated cyclic hydrocarbon structure, such as cyclohexyl, cyclopropyl, cyclobutyl, cyclopentyl and cycloheptyl;

"cycloalkenyl" is a cyclic hydrocarbon structure containing at least one double bond and includes substituted aryl groups, such as 1,2-, 1, 3-and 1,4-phenylene;

"pseudopeptide" is an entity which is partially amino acid (peptidic) in nature and partially organic chemical in nature;

"alkenyl" and "olefin" are interchangeably defined herein as a hydrocarbon structure containing at least one double bond, suitable alkenyls can also be hydrocarbon structure containing multiple double bonds, the double bonds can optionally be incorporated into a ring structure, such as a cycloalkenyl;

"amino acid linkage" is exemplified by a moiety having a N-terminal amino group and a C-terminal carbonyl group;

"alkyl" is a paraffinic hydrocarbon group which may be derived from an alkane by dropping one hydrogen from the formula, such as methyl, ethyl, propyl, isopropyl, butyl, and so forth;

"substituted $C_1$–$C_6$ alkyl" is a branched alkyl, such as methylbutyl;

"aryl" is an aromatic ring compound such as benzene, phenyl, naphthyl;

"substituted aryl" is a substituted aromatic ring including, but not limited to, alkyl substitution, or halogen substitution; and "aralkyl" is a aryl being attached through an alkyl chain, straight or branched, containing from one through six carbons, such as a phenylpropyl group.

A "direct bond" is a bond which replaces a particular amino acid compound between adjacent amino acids and which amino acid may also be indicated to be absent by the term "null".

The phrase "a suitable amine protecting group" is a group, such as Boc (t-butyloxycarbonyl-) which protects the amine moiety from reaction and which can be removed under mild conditions so as not to affect the rest of the molecule.

Definitions of the amino acid abbreviations used herein are as follows:

"aromatic amino acid" is a naturally occurring or non-naturally occurring amino acid having one or more unsaturated carbon rings and includes, but is not limited to, Phe, Tic, Thi, N-benzyl Gly, Tyr, Trp.

Arg is arginine; Ala is alanine; Aib is 2-aminoisobutyric acid; Aoc is (S,S,S)-2-azabicyclo[3.3.0]octane-3-carboxylic acid; Asn is asparagine; Asp is aspartic acid; Cys is cysteine; Eac is ε-aminocaproic acid; Gln is glutamine; Glu is glutamic acid; Gly is glycine; Ile is isoleucine; Leu is leucine; Lys is lysine; Met is methionine; Nal is beta-2-naphthylalanine; Orn is ornithine; Pro is proline; dehydroPro is 3,4-dehydroproline, homoPhe is homophenylalanine; 4Hyp is 4-hydroxyproline; Ser is serine; Sar is sarcosine; Thi is beta-2-thienylalanine; Thr is threonine; Thz is thiazolidine-4-carboxylic acid; Phe is phenylalanine; phenylGly is 2-phenylglycine; Tic is tetrahydroisoquinoline-3-carboxylic acid; Oic is (2S, 3aS, 7aS)-octahydro-1H-indole-2-carboxylic acid; Val is valine; phenyl is a 3-methyl-2-butenyl radical. D-Hype (trans-propyl) is 4S-D-prolyl propyl ether and represents

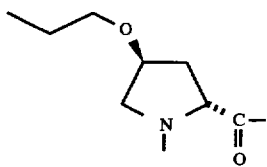

D-Hype (trans-thiophenyl) is 4S-D-prolyl phenyl thioether, also known as D-4-hydroxyproline trans phenylthioether also known as D-Hyp S(trans phenyl) and represents

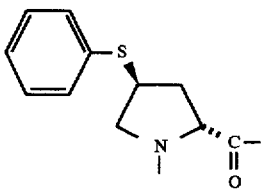

D-Hype (trans-phenylpropyl) represents

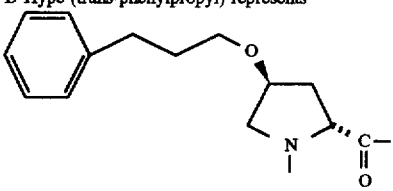

D-Hype (trans-2-methylbutyl) represents

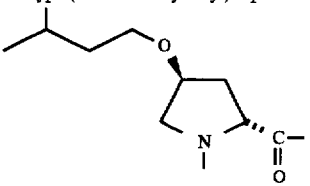

D-Hype (trans-ethyl) represents

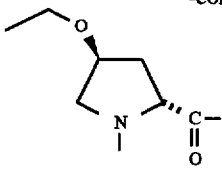

D-Hype (trans-methyl) represents

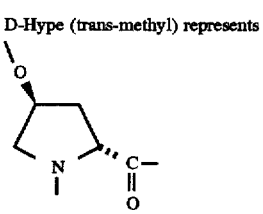

Aoc can be prepared by the method of V. Teetz, R. Geiger and H. Gaul, Tetrahedron Lett. (1984), 4479. Tic can be prepared by the method of K. Hayashi, Y. Ozaki, K. Nunami and N. Yoneda, Chem, Pharm. Bull. (1983) 31,312.

All amino acids residues, except Gly and Sar, described in the specification are preferably of the L-configuration unless otherwise specified. It would be recognized, however, that the 7 position amino acids and derivatives must always be the D-configuration whereas the amino acids and derivatives of position 8 may be either in the D- or L- configuration. The hydroxyproline ethers at position 7 are preferably in a trans configuration, whereas the hydroxyproline ethers at position 8 can be in either the cis or trans configuration. The symbols and abbreviations used for amino acids, their derivatives and protecting groups, and peptides and their salts are those customarily used in peptide chemistry. (See Biochem. J. (1972), 126, 773), which Journal reference is hereby incorporated by reference.

The synthesis of the peptides of this invention including derivation, activation, and coupling of protected amino acid residues, and their purification, and the analytical methods for determining identity and purity are included in the general body of knowledge of peptide chemistry, as described in Houben Weyl Methoden der Organischen Chemie, (1974), Vol. 16, parts I & II for solution-phase synthesis, and in Solid Phase Peptide Synthesis. (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate hydroxyproline substituents used at position 7 or 8 are prepared by the process described in PCT publications WO 92/18155 and WO 92/18156 which are herein incorporated by reference. The starting materials are commercially available and can be prepared by known procedures. Both the cis and trans stereoisomers can be prepared by these means and are within the scope of the present invention.

The substituents used to replace the amino acids at positions 2 through 5 are prepared using various conventional chemical synthesis procedures that are well known to those skilled in the art. Various general prototypic sequences are outlined in Schemes I and II.

The preparation of compounds for administration in pharmaceutical preparations may be performed in a variety of methods well known to those skilled in the art. Appropriate pharmaceutically acceptable salts within the scope of he invention are those derived from mineral acids such as hydrochloric acid, hydrobromic acid, phosphoric acid, nitric acid, and sulfuric acid; and organic acids such as tartaric acid, fumaric acid, lactic acid, oxalic acid, methanesulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively.

The compounds of the invention contain asymmetric carbon atoms. Thus, the invention includes the individual stereoisomers, and the mixtures thereof. The individual isomers may be prepared or isolated by methods known in the art.

ADMINISTRATION AND USE

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include inflammatory disorders such as shock, systemic inflammatory response syndrome, pancreatitis, and gioedema, arthirtis, inflammatory bowel disease, systemic treatment of pain and inflammation, and local trauma such as wounds, burns, rashes airway disorders such as asthma, rhinitis and allergies, and nervous system diseases such as spinal cord injury, stroke, hemorrhage, trauma, tumors, abcess and encephalitis. The compounds of the invention which are $B_1$ receptor antagonists are useful, alone or in combination with the $B_2$ receptor antagonists of the invention, for the treatment of conditions associated with persistent inflammatory hyperalgesia, e.g. rheumatoid arthritis.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. Other pharmaceutically acceptable agents and formulations which are known to those skilled in the pharmaceutical art may be used.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs are suitably prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 500 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, intraveneously, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel compounds are potent, selective bradykinin receptor antagonists.

Preparation of an N-Boc protected substituted ω-aminoalkanoic acid for introduction of the group E (wherein X is an imino group) of the pseudopeptides of this invention is illustrated by the synthesis of N-Boc-5-amino-2-benzyl-3-pentenoic acid (10) as outlined in Scheme I.

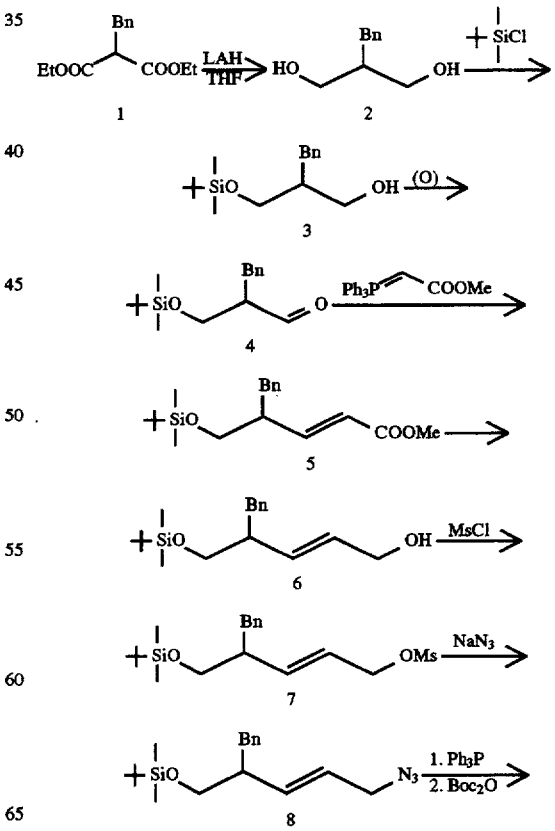

-continued
Scheme I

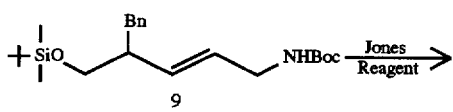

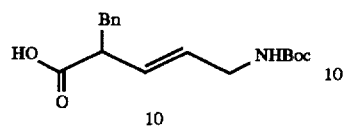

Accordingly, diethyl benzylmalonate (1) is reduced with lithium aluminum hydride to afford 2-benzyl-1,3-propanediol (1) which is treated with an equimolar amount of tert-butyldimethylsilyl chloride to give the monoprotected alcohol 3. Swern (dimethylsulfoxide/oxalyl chloride) oxidation of 3 provides the aldehyde 4 which is condensed with the Wittig reagent methyl (triphenylphosphonylidene) acetate to give 6. Conversion of the alcohol 6 to the mesylate 7 followed by azide displacement affords 8 which is sequentially reduced and Boc protected to give 9. Jones oxidation of the tert-butyldimethylsilyl ether 9 provides the Boc protected subsituted ω-aminoalkenoic acid 10.

By alteration of the benzyl substituent of the malonate starting material the group Y of the general structure E may be varied. Modification of the reagent employed for Wittig condensation with the aldehyde, e.g., 4, enables variation of $Z_1$, $Z_2$, m, n, and o of the aminoalkenoyl group E that is introduced into the pseudopeptides of this invention.

The general method utilized to prepare mono- and poly-olefinic substituted ω-(2-pyrrolidinyl)alkenoic acids for introduction of the fragments wherein D is 2-pyrrolidinyl and E is an alkenoyl group into the pseudopeptides of this invention is illustrated by the synthesis of (2S-2S-benzyl-7-(2S-pyrrolidinyl)-6-heptenoic acid (18) as outlined in Scheme II. Substituted ω-(2-pyrrolidinyl)alkanoic acids 19 are obtained by catalytic hydrogenation of olefinic precursors as shown in Scheme II.

Scheme II

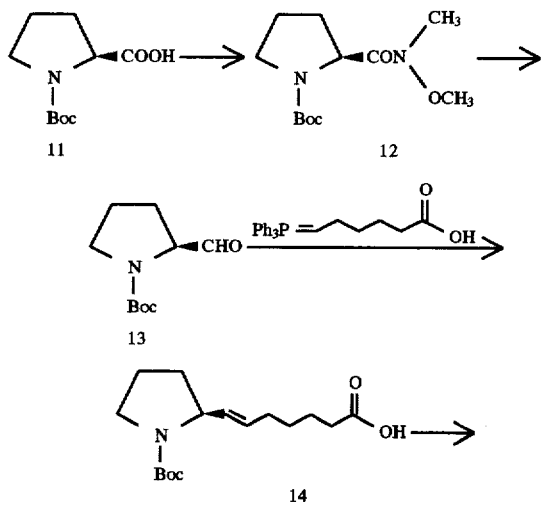

-continued
Scheme II

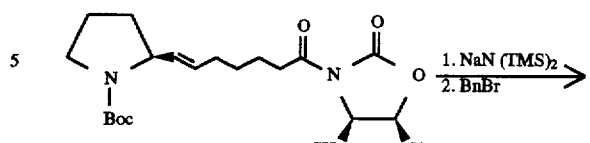

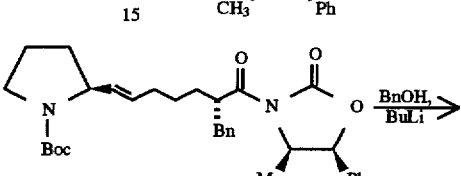

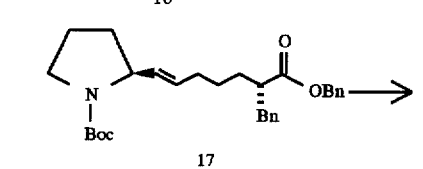

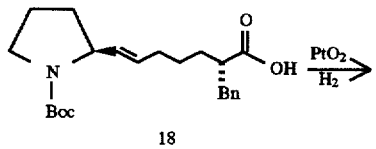

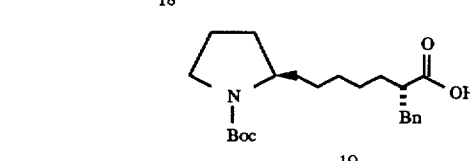

The initial step in this sequence involves conversion of Boc-protected L(S)-proline (11) to 2-pyrrolidinecarboxaldehyde (13) via Boc-protected N-methoxyl-N-methyl-L-prolinamide (12) according to previously described nethodology [Fehrentz, J. A. and Castro, B. Synthesis (1983) 676–678; Hocart, S. J., et al. J. Med. Chem. (1988) 31, 1920–1824; Nahm, S. and Weinreb, S. M. Tet. Lett. (1981) 22, 8315-3818]. Condensation of 13 with the Wittig reagent derived from 6-bromohexanoic acid and triphenylphosphine according to the general method of Corey, H. S., Jr. et al. [J. Am. Chem. Soc. (1964) 86, 1884] produced Boc-protected 7-(2-pyrrolidinyl)-6-heptenoic acid (14) which is stereoselectively benzylated via the chiral amide 15 to produce 16 according to a previously described general procedure [Mavunkel, B. J., et al. Tet. Lettr. (1993), 14, 2225]. Alcoholysis of the amide with benzyl alcohol gives the ester 17 which is hydrolyzed to 18 according to the procedure of Evans, D. R., et al. [J. Org. Chem. (1985) 50, 1930- 1835]. Hydrogenation of 18 results in the saturated benzyl-substituted ω-(2-pyrrolidinyl)alkanoic acid 19.

By varying the Wittig reagent and the halide employed for alkylation of the chiral amide employed in the described sequence (Scheme II) substituted pyrrolidinylalkenoic acids and pyrrolidinylalkanoic acids that enable synthesis of pseudopeptides of this invention in which the D–E fragment incorporates the described Y, $Z_1$, $Z_2$, n, m and o values are obtained.

The following examples are illustrative of preferred embodiments of methods of preparation and compounds of the invention and are not to be construed as limiting the invention thereto.

EXAMPLES

The synthesis of the peptides of this invention including derivation, activation, and coupling of protected amino acid residues, and their purification, and the analytical methods for determining identity and purity are included in the general body of knowledge of peptide chemistry, as described in Houben Weyl Methoden der Organischen Chemie, (1974), Vol. 16, parts I & II for solution-phase synthesis, and in Solid Phase Peptide Synthesis, (1984), by Stewart and Young for synthesis by the solid phase method of Merrifield.

The substituents used to replace the amino acids at positions 2 through 5 are prepared using various conventional chemical synthesis procedures that are well known to those skilled in the art. Various general sequences are outlined in Schemes I and II.

Any chemist skilled in the art of peptide synthesis can synthesize the peptides of this invention by standard solution methods or by manual or automated solid phase methods.

EXAMPLE 1

N-Boc-5-Amino-2-benzyl-3-pentenoic Acid (10)

The overall procedure for synthesis of 10 for diethyl benzylmalonate is outlined in Scheme I.

1. Preparation of 2-benzyl-1,3-propanediol (2). To a stirred solution of 3.80 g (100 mmol) of lithium aluminum hydride in 200 ml of tetrahydrofuran at 0° C. was added dropwise a solution of 11.61 g (46.4 mmol) of diethyl benzylmalonate in 100 ml of tetrahydrofuran. After being stirred at 0° C. for 3 hours, the reaction mixture was quenched by cautious dropwise addition of 50 ml of 1N hydrochloric acid followed by 100 ml of water. The mixture was extracted with ethyl acetate. The extracts were dried and concentrated to afford 6.94 g (90%) of a white crystalline solid; $^1$H NMR (CDCl$_3$) δ 1.97 (m, 1H), 2.45 (s, 2H), 2.82 (s, 2H), 3.55 (m, 2H), 3.70 (m, 2H), 7.05 (m, 3H), 7.18 (m, 2H).

2. Preparation of 3-(tert-Butyldimethylsilyloxy)-2-benzylpropanol (3). A solution of 6.92 g (41.6 mmol) of the diol 2 in 100 ml of tetrahydrofuran was added slowly to a stirred suspension of 2.01 g (87.4 mmol) of sodium hydride in 200 ml of tetrahydrofuran. After the mixture was stirred for 2 hours, a solution of 6.27 g (41.6 mmol) of tert-butyldimethylsilyl chloride in 50 ml of tetrahydrofuran was added dropwise. The mixture was stirred for 20 hours and then it was quenched by adding 100 ml of a saturated aqueous solution of ammonium chloride and extracted with ethyl acetate. The extracts were dried and concentrated. The residue was flash chromatographed (50% ethyl acetate/hexane) to give 9.04 (77% yield) of 3 as a colorless liquid; $^1$H NMR (CDCl$_3$) δ0.05 (s, 6H), 0.92 (s, 9H), 1.94 (m, 1H), 2.39 (m, 1H), 2.50 (d, 2H), 3.55 (m, 2H), 3.63 (m, 2H), 7.03 (m, 3H), 7.12 (M, 2H); IR (neat) 3406, 2915, 1470, 1255, 1100, 843 cm$^{-1}$.

3. preparation of 3-(tert-Butyldimethylsilyloxy)-2-benzylpropanal (4). Dimethylsulfoxide (3 ml) was added dropwise to a solution of 1.10 g (8.67 mmol) of oxalyl chloride in 30 ml of methylene chloride at −78° C. This solution was stirred and a solution of 2.08 g (7.42 mmol) of the propanol it in 10 ml of dimethylsulfoxide was added. The resulting mixture was stirred for 20 minutes and then 7.6 ml (54.4 mmol) of triethylamine was added. After being stirred for an additional 20 minutes, the mixture was poured into 100 ml of water. The layers were separated. The aqueous phase was extracted with methylene chloride. The combined organic phases were dried and concentrated. The residue was purified on a silica gel column with 3:2 ether/hexane to give 1.84 g (90%) of 3 as a colorless liquid; $^1$H NMR (CDCl$_3$) δ0.12 (s, 6H), 0.91 (s, 9H), 2.60 (m, 1H), 2.71 (m, 1H), 2.98 (m, 2H), 3.63 (m, 1H), 3.81 (m, 1H), 7.09 (m, 5H); IR (neat); 2931, 2860, 1730, 1471, 1255, 1100, 846 cm$^{-1}$.

4. Preparation of Methyl 4-Benzyl-5-(tert-butyldimethylsilyloxy)-2-pentenoate (5). A solution of 900 mg (3.24 mmol) of the propanal 4 and 1.21 g (3.56 mmol) of methyl (triphenylphosphonylidene) acetate in 30 ml of acetonitrile was heated under reflux for 5 hours. The mixture was concentrated in vacuo and the residue was flash chromatographed to give 900 mg (83%) of ester 5 as a colorless liquid; $^1$H NMR (CDCl$_3$) δ0.12 (s, 6H), 1.02 (s, 9H), 2.75 (m, 2H), 3.02 (m, 1H), 3.69 (d, 2H), 3.83 (s, 3H), 5.88 (d, 1H, J=15.6 Hz), 7.03 (m, 1H, J=7.9, 15.6 Hz), 7.39 (m, 5H); IR (nuyol) 2951, 2931, 2847, 1728, 1471, 1435, 1247, 1103, 838 cm$^{-1}$.

5. Preparation of 4-Benzyl-5-(tert-butyldimethylsilyloxy)-2-pentanol (6). Disobutylaluminum hydride (11 ml of a 1.5M solution in toluene, 16.3 mmol) was added to a stirred solution of the ester 5 (2.18 g, 6.52 mml) in 20 ml of toluene. After the mixture was stirred at −78° C. for 1 hour it was quenched by addition to saturated aqueous ammonium chloride. The mixture was extracted with ethyl acetate. The extracts were dried and concentrated to give 1.80 g (90%) of crude alcohol fi as an oil; $^1$H NMR (CDCl$_3$) δ0.12 (s, 6H), 0.98 (s, 9H), 1.22 (br s, 1H), 2.59 (m, 2H), 2.85 (m, 1H), 3.45 (m, 2H).3.95 (m, 2H), 5.59 (m, 2H), 7.11 (m, 3H), 7.20 (m, 2H); IR (neat) 3409, 2954, 2929, 2847, 1471, 1200, 836 cm$^{-1}$.

6. Preparation of 4-Benzyl-5-(tert-butyldimethylsilyloxy)-2-pentenyl Mesylate (7). Methanesulfonyl chloride (1.68 g, 14.68 mmol) was added dropwise to a stirred solution of the alcohol 6 (1.80 g, 5.87 mmol) and 3.8 ml (14.68 mmol) of triethylamine in 20 ml of methylene chloride at 0° C. Th mixture was stirred for 1 hour and then 100 ml of water was added. The layers were separated. The aqueous layer was extracted with methylene chloride. The combined organic layers were dried and concentrated to afford a viscous oil; $^1$H NMR (CDCl$_3$) δ0.06 (s, 6H), 0.88 (s, 9H), 2.52 (m, 2H), 2.80 (s, 3H), 2.85 (m, 1H), 3.11 (d, 2H), 4.61 (d, 2H), 5.53 (m, 1H), 5.64 (m, 1H), 7.12 (m, 3H), 7.23 (m, 2H); IR (neat) 2942, 2859, 1471, 1355, 1252, 1175, 1100, 934, 838 cm$^{-1}$.

7. Preparation of 5-Benzyl-5-(tert-butyldimethylsilyloxy)-2-pentenylazide (8). A mixture of 2.14 g (5.56 mmol) of the mesylate 7 and 543 mg (8.35 mmol) of sodium azide in 50 ml of dimethylformamide was stirred at 25° C. for 16 hours. The reaction mixture was poured into 200 ml of water and the resulting mixture was extracted with ether. The ether extracts were dried and concentrated to give 1.05 g of the crude azide 8 as an oil that was employed for further reaction without purification.

8. Preparation of 5-Benzyl-N-Boc-5-(tert-butyldimethylsilyloxy)-2-pentenylamine (9). After a mixture of 1.05 g of the crude azide 8 and 1.25 g (4.76 mmol) of triphenylphosphine in 20 ml of tetrahydrofuran and 5 ml of water was stirred at 25° C. for 16 hours, 1.45 g (6.66 mmol) of di-tert-butyl dicarbonate was added and the stirred mixture was heated at 70° C. for 1 hour. The reaction mixture was concentrated in vacuo and the residue was purified by flash chromatography utilizing 20% ethyl acetate in hexane to afford 1.09 g (85%) of 9 as a viscous oil; $^1$H NMR (CDCl$_3$) δ0.10 (s, 6H), 0.85 (s, 9H), 1.45 (s, 9H), 2.51 (m, 1H), 2.58 (m, 1H), 2.83 (m, 1H), 3.42 (m, 2H), 3.59 (br s, 2H), 4.30 (br s, 1H), 5.22 (m, 1H), 7.08 (m, 5H); IR (neat) ee50, 2926, 1707, 1500, 1252, 1172, 1103, 835 cm$^{-1}$.

9. Preparation of N-Boc-5-amino-2-benzyl-3-pentenoic Acid (10). To a stirred solution of the Boc-protected amine 9 (1.70 g, 4. 19 mmol) in 100 ml of acetone at 0° C. was added 6.5 ml of a 2.3M solution of chromium trioxide in aqueous sulfuric acid. After being stirred for 3 hours at 0° C., the mixture was diluted with 100 ml of water and extracted with ether. The ether extracts were extracted with two 50 ml portions of 2 N NaOH. The basic extracts were acidified with 10% aqueous citric acid solution and the mixture was extracted with ethyl acetate. After being dried, the extracts were concentrated to leave a solid residue. Recrystallization from ethyl acetate afforded 340 mg (27%) of the Boc-protected amino acid 10; $^1$H NMR (CDCl$_3$) δ1.42 (s, 9H), 2.80 (m, 1H), 3.08 (m, 1H), 3.25 (m, 1H), 3.62 (m, 2H), 4.49 (br s, 1H), 5.42 (m, 1H), 5.62 (m, 1H), 7.21 (m, 5H); IR (nujol) 3337, 2975, 1710, 1661, 1252, 1165 cm$^{-1}$.

The procedure of this Example is varied by modification of the malonate starting material 1 and the Wittig reagent employed for condensation with the aldehyde, e.g., 4, to provide other protected aminoalkenoic acids required for introduction of the aminoalkenoyl group E with varied $Z_1$, $Z_2$, m, n and o values into pseudopeptides of this invention.

EXAMPLE 2

2S-Benzyl-7-(N-Boc-2S-pyrrolidinyl)-6-heptenoic Acid (19)

The overall procedure for synthesis of 19 from N-Boc-L-(S)-proline (11) is outlined in Scheme II.

1. Preparation of N-Boc-N'-methoxy-N'-methyl-(S)-prolinamide (12). 1-(3-Dimethylaminopropyl)-3-ethylcarbodiimide hydrochloride (16.75 g, 85.6 mmol), triethylamine (21.1 g, 209 mmol) and several drops (a catalytic amount) of 4-dimethylaminopyridine were added to a stirred mixture of 15.01 g (69.7 mmol) of N-Boc-L-proline and 7.52 g (75.5 mmol) of N,O-dimethylhydroxylamine hydrochloride in 150 ml of methylene chloride at 0° C. After the mixture was stirred at 25° C. for 20 hours it was washed successively with water and brine, dried over sodium sulfate and concentrated to provide 17.47 g (97% yield) of 12 as a colorless oil; $^1$H NMR (CDCl$_3$) δ1.42 (s, 9H), 2.00 (m, 4H), 3.19 (s, 3H), 3.50 (m, 2H), 3.72 (s, 3H), 4.66 (m, 1H).

2. Preparation of N-Boc-2S-pyrrolidinecarboxaldehyde (13). Lithium aluminum hydride (1.15 g, 28.4 mmol) was added in small portions over a period of 30 minutes to a stirred solution of 5.88 g (22.76 mmol) of 2 in 100 ml of ether at 0° C. After the mixture was stirred at 0° C. for 1.5 hours 50 ml of 10% aqueous potassium bisulfate solution was added dropwise and with caution. The mixture was separated and the aqueous part was extracted with ether. The combined ether solution and extracts were washed successively with 0.3N HCl, saturated aqueous sodium bicarbonate solution and brine, dried over sodium sulfate, and concentrated to give 4.35 g (96% yield) of 13 as a colorless liquid; $^1$H NMR (CDCl$_3$) δ1.43 (s, 9H), 1.95 (m, 4H), 3.45 (m, 2H), 4.10 (m, 1H), 950 (s, 1H).

3. Preparation of N-Boc-7-(2S-pyrrolidinyl)-6-heptenoic Acid (14). Sodium hydride (2.89 g, 96 mmol) was added, in portions over a period of 30 minutes, to a stirred mixture of 8.0 g (40 mmol) of 13 and 22.4 g (40 mmol) of 6-(triphenylphosphonium) hexanoic acid bromide (prepared from equimolar amounts of triphenylphosphine and 6-bromohexanoic acid), in 100 ml of tetrahydrofuran and 100 ml of dimethylsulfoxide at 0° C. After the mixture was stirred at 0° C. for 4 hours, 100 ml of saturated aqueous ammonium chloride solution was added. The mixture was concentrated to remove tetrahydrofuran. Water (100 ml) was added and the mixture was extracted with ethyl acetate. The organic extracts were washed with water and brine, dried (Na$_2$SO$_4$) and concentrated. The residue was chromatographed on a column of silica gel using ethyl acetate:hexane 3:7 to afford 5.11 g (45% yield) of 14 as a colorless liquid; $^1$H NMR (CDCl$_3$) δ1.42 (m, 9H), 1.65 (m, 3H), 1.82 (m, 3H), 2.07 (m, 2H), 2.15 (m, 2H), 3.37 (m, 3H), 4.42 (br s, 1H),5.30 m, 2); [α]$_D^{25}$=+5.3° (c=1.16, CH$_2$Cl$_2$).

4. Preparation of 1-[7-(n-Boc-2S-pyrrolidiny)-6-heptenoyl]-5R-methyl-4R-phenyl-2-oxazolidinone (15). Triethylamine (1.00 g, 9.93 mmol) and 1.20 g (9.93 mmol) of pivaloyl chloride were added to a stirred solution of 2.81 g (9.46 mmol) of 14 in 125 ml of ether at −78° C. After the resulting mixture was stirred at −78° C. for 5 minutes and then at 0° C. for 1 hour, a solution prepared by adding 9.93 mmol of n-butyllithium to 1.67 g (9.46 mmol) of 5R-methyl-4R-phenyl-2-oxazolidinone in 40 ml of tetrahydrofuran at −78° C. followed by stirring at −78° C. for 10 minutes, was added at −78° C. After the mixture was stirred at −78° C. for 40 minutes and at 0° C. for 30 minutes, 50 ml of a saturated aqueous solution of ammonium chloride was added. After the organic solvents were removed by concentrating the mixture, it was extracted with ethyl acetate. The extracts were washed with brine, dried over sodium sulfate and concentrated. The residue was chromatographed on a silica gel column eluting with ethyl acetate:hexane 1:9 to give 2.92 g (67.8% yield) of 15 as a colorless liquid; $^1$H NMR (CDCl$_3$) δ0.89 (d, 3H, J=6.7 Hz), 1.43 (s, 9H), 1.70 (m, 6H), 2.20 (m, 4H), 2.97 (m, 2H), 3.38 (m, 2H), 4.50 (m, 1H), 4.76 (m, 1H), 5.34 (m, 2H), 5.67 (d, 1H, J=7.3 Hz,) 7.40 (m, 5H); IR (neat) 2972, 1782, 1738, 1697, 1455, 1393, 1167, 768, 702 cm$^1$.

5. Preparation of 1-[2S-benzyl-7-(N-Boc-2S-pyrrolidinyl)-6-heptenoyl]-5R-methyl-4R-phenyl-2-oxazolidine (16). Sodium bis (trimethylsilyl)amide (85.8 ml of 1M solution in tetrahydrofuran, 8.58 mmol) was added dropwise to a stirred solution of 3.26 g (7.1 mmol) of the chiral amide 15in 150 ml of tetrahydrofuran at −78° C. The solution was stirred at −78° C. for 30 minutes and then 3.67 g (71.4 mmol) of benzyl bromide was added. The resulting mixture was stirred at −78 ° C. for 3 hours and then 50 ml of a saturated aqueous solution of ammonium chloride was added. After the mixture was concentrated to remove tetrahydrofuran, it was extracted with ethyl acetate. The extracts were washed with brine, dried and concentrated. The residue was chromatographed on silica gel eluting with ethyl acetate:hexane 1:9 to provide 2.29 g (59% yield) of 16 as a colorless liquid; $^1$H NMR (CDCl$_3$) δ0.60 (d, 3H, J=6.7 Hz), 1.41 (m, 9H), 1.70 (m, 6H), 2.20 (m, 4H), 2.79 (dd, 1H, J=13.3, 7.4 Hz), 3.00 (dd, 1H, J=13.3, 7.6 Hz), 3.39 (m, 2H), 4.25 (m, 1H), 4.48 (m, 1H), 4.48 (m, 1H), 4.75 (m, 1H), 5.34 (m, 2H), 5.60 (d, 1H, 1=7.3 Hz), 7.30 (m, 10H); [α]$_D^{25}$=+22.9° (c=0.85, CH$_2$Cl$_2$); IR (neat) 2975, 2931, 1782, 1740, 1697, 766, 702 cm$^{-1}$.

6. Preparation of Benzyl 2S-Benzyl–7-(N-Boc-2S-pyrrolidinyl)-6-heptenoate (17). A solution of n-butyllithinm (29.2 ml, 1.6M in hexane, 4.67 mmol) was added dropwise over a period of 10 minutes to a stirred solution of 0.67 g (6.23 mmol) of benzyl alcohol in 50 ml of tetrahydrofuran at 0C. After the mixture was stirred at 0° C. for 20 minutes, a solution of 2.29 g (4.19 mmol) of 16 in 50 ml of tetrahydrofuran was added slowly and stirring was continued for 3.5 hours at 0° C. After addition of 50 ml of a saturated aqueous solution of ammonium chloride, the mixture was concentrated to remove tetrahydofuran. The mixture was extracted with ethyl acetate. The extracts were washed with brine, dried, and concentrated. Chromatography of the residue (silica gel, ethyl acetetate: hexane 1:9) afforded 0.98 g (66% yield) of 17 as a colorless oil; $^1$H NMR (CDCl$_3$) δ1.40 (m, 11H), 1.80 (m, 8H), 2.75 (m, 2H), 2.92 (m, 1H), 3.40 (m, 2H), 4.41 (m, 1H), 5.00 (s, 2H), 5.33 (m, 2H), 7.22 (m, 10H); [α]$_D^{25}$=+14.8° (c=1.0, CH$_2$Cl$_2$); IR (neat) 3188, 2928, 1733, 1697, 1393, 1167, 699 cm$^{-1}$.

7. preparation of 2S-Benzyl-7-(N-Boc-2S-pyrrolidinyl)-6-heptenoic Acid (18). A solution of 0.83 g (1.74 mmol) of 17 and 5 ml of 30% HBr in acetic acid was stirred at 50° C. for 15 minutes. Water (60 ml) was added, the pH was adjusted to 10 with sodium carbonate, and then a solution of 1.40 g (6.4 mmol) of di-tert-butyl dicarbonate in 50 ml of 2-propanol was added. After the mixture was stirred at 25° C. for 1 hour, it was concentrated to remove 2-propanol, cooled to 0° C. and adjusted to pH 3 with 1N HCl. The mixture was extracted with ethyl acetate. The extracts were washed with brine, dried (Na$_2$SO$_4$) and concentrated. Chromatography (silica gel, ethyl acetate:hexane 2:8) gave 0.42 g (63% yield) of 18 as a colorless liquid; $^1$H NMR (CDCl$_3$) δ1.42 (m, 10H), 1.60 (m, 5H), 1.80 (m, 2H), 2.06 (m, 2H), 2.75 (m, 3H), 2.95 (m, 1H), 3.37 (m, 2H), 4.50 (m, 1H), 5.32 (m, 2H), 7.18 (m, 5H); [α]$_D^{25}$=+14.8° (c=1.0, CH$_2$Cl$_2$); IR (neat) 3188, 2928, 1733, 1697, 1393, 1167, 699 cm$^{-1}$. Anal. Calcd. for C$_{23}$H$_{33}$NO$_4$: C, 71.29; H, 8.58; N, 3.61. found: C, 71.32; H 8.62; N, 3.64.

By modifying the Wittig reagent employed for preparation of 14 as described in this Example various pyrrolidinylalkenoic acids that enable the synthesis of the pseudopeptides of this invention in which the D–E fragments have the appropriate Z$_1$, Z$_2$, n, m, and o values are obtained.

Thus, Boc-protected 4-(2-pyrrolidinyl)-3-butenoic, 8-(2-pyrrolidinyl)-7-octenoic, and 9-(2-pyrrolidinyl-8-nonenoic acids were prepared as colorless oils when 3-bromopropanoic, 7-bromoheptanoic and 5-bromooctanoic acids, respectively, were employed for preparation of the Wittig reagent that was condensed with N-Boc-2-pyrrolidinecarboxaldehyde as described in this Example.

Replacement of benzyl bromide alkylating reagent utilized to alkylate the chiral alkenoic acid amide, e.g., the conversion 15 to 16, enables variation of the subsstitutent Y in the substituted Boc-protected pyrrolidinylalkenoic acids as required for incorporation of the defined D–E fragments of pseudopeptides of this invention.

EXAMPLE 3

This conversion is illustrated in Scheme II.

2S-Benzyl-7-(N-Boc-2S-pyrrolidinyl)heptanoic Acid (19)

A mixture of 54.6 mg (1 mmol) of 18 and 50 mg of platinum oxide in 100 ml of ethanol was hydrogenated by shaking on a Parr apparatus at 25° C. under an initial pressure of 50 p.s.i. of hydrogen. After hydrogen uptake was completed in about 1 hour, the reaction mixture was filtered. The filtrate was concentrated to give 49.3 mg (90% yield) of 19 as a colorless oil.

This procedure is also employed to prepare aminoalkanoic and pyrrolidinylalkanoic acid precursors for the defined D–E fragments (where Z$_1$ and Z$_2$ represent a direct bond) of the pseudopeptides of this invention.

EXAMPLE 4

B$_2$ Receptor Antagonist Peptide Synthesis

The pseudopeptides listed in Table I were synthesized manually using standard solid phase methods and t-Boc chemistry.

1. Boc-Arg(Tos)-PAM resin was used for the purpose. Amino acids and Boc-protected derivatives of aminoalkanoic acids and related olefins prepared as described in Examples 1–3 were introduced according to the sequence of the pseudopeptide.

2. Deprotection: The N-terminal t-Boc protection was accomplished by treating the resin-aa/resin-peptide with trifluoroacetic acid/methylene chloride (1:1) for two minutes followed by a similar treatment for 30 minutes.

3. The resin was then washed with methylene chloride and ethanol and neutralized with 10% triethylamine/methylene chloride or 10% diisopropylethylamine/methylene chloride.

4. Couplings: All couplings were carried out using the active ester of the amino acid. The active esters of the individual amino acids were generated prior to their introduction into solid phase synthesis. Five equivalents (with respect to loading of the first amino acid on the resin) of the amino acid, hydroxybenzotriazole hydrate and dicyclohexylcarbodiimide or diisopropylcarbodiimide, was incubated for 30 minutes at 0° C. in dimethyl formamide or methylene chloride/dimethyl formamide (1:1) for this purpose. Couplings were followed until no more free amine was detected on the resin using qualitative ninhydrin analysis (Kaiser test). Different un-natural amino acids behave differently during ninhydrin analysis and the color of the resin (after deprotection and coupling) depends on the specific amino acid being used.

5. After coupling, the resin-peptide was washed with dimethylformamide and methylene chloride before commencement of another cycle of the synthesis.

6. The finished peptidyl-resin was cleaved from the resin using HF (10 mL/g of resin) in the presence of 10% anisole (scavenger). After removal of HF, the peptide resin was washed with ether and the peptide was extracted with 0.1% TFA or 0.2% acetic acid. Lyophilization yielded crude peptide, usually flaky yellow solids were obtained at this stage.

7. The crude peptide was purified using reverse phase high performance liquid chromatography on a C$_{18}$ column using a gradient of water/acetonitrile (both containing 0.1% trifluoroacetic acid or 0.2% acetic acid). The pure fractions were determined by analytical HPLC, on a Vydac C$_{18}$ column using a gradient of water/acetonitrile (both containing 0.1% trifluoroacetic acid) and pooled together and lyophilized to give flaky white solids.

8. Peptides were analyzed by analytical reverse phase HPLC on a Vydac C$_{18}$ column using a gradient of water/acetonitrile (both containing 0.1% trifluoroacetic acid), and fast atom bombardment mass spectroscopy.

EXAMPLE 5

Preparation of B$_1$ Receptor Antagonists

The B$_1$ receptor antagonism corresponding to the pseudopeptide of Table I, wherein the C-terminal arginine is deleted, are prepared in a manner analogous to that described in Example 4. The solid phase synthesis is initiated using Boc-Oic-PAM, resin obtainable from a commercial supplier (Advanced Chemtech, Louisville, Ky.).

EXAMPLE 6

Bradykinin Binding Procedures

Guinea Pig Ileum Binding

Binding of 3H-bradykinin was performed using the method of D. C. Manning, R. Vavrek, J. M. Stewart, and S.

H. Snyder, J. Pharmacol. Exp. Ther., (1986), 237, 504. The tissues used in the binding assay were terminal ileum from male Hartley guinea pigs (150–350 g). After dissection, tissues were placed in 20 volumes of ice-cold buffer A (25 mM TES containing 0.2 g/l of 1,10-phenanthroline adjusted of pH 6.8 with ammonium hydroxide) and homogenized using a Ploytron Tissumizer at setting 6 for 15 seconds. The homogenate was centrifuged at 50,000×g for 10 minutes, the supernatant discarded, and the pellet resuspended in ice-cold buffer A by homogenization with the Polytron. Each tissue was homogenized and centrifuged three times.

The final pellet was resuspended in buffer A containing bovine serum albumin (1 g/l) and Bacitracin (0.14 g/l) to a final volume of 170 ml/g of the original tissue weight. The binding assay consisted of 1 mM in 12×75 mm polypropylene tubes: 50 µl $^3$H-bradykinin (20,000 dpm, ~0.3 nM in the final assay volume), 100 µl displacing drug in buffer A, and 750 µl tissue homogenate. Each tray contained tubes, to which no drug was added to measure maximum binding and tubes to which bradykinin (1 µM final concentration) had been added, to measure specific binding. Specific binding accounted for 96–98% total binding. Tubes were incubated for 90 minutes at ambient temperature. The assays were terminated by filtration over Whatman GF/B glass fiber filters that had been pretreated for 2 hours with polyethyleneimine (2g/l) using a Brandel Tissue Harvester, followed by washing with 4×1 ml aliquots of ice-cold 50 mM Tris, pH 7.4. Filters were dissolved in Ready-Safe Fluor (Beckman) for at least 90 minutes before quantitation by liquid scintillation spectrometry. Kd values were determined using saturation binding and analysis by EBDA (G. A. MacPherson, J. Pharmacol. Methods, (1985), 213), followed by LIGAND (P. J. Munson, D. Rodbard, Anal. Biochem,. (1980), 220). $K_i$ values were determined using competitive analysis followed by EBDA and LIGAND. The test results obtained are shown in Table I.

Human Bradykinin Receptor Binding

The human bradykinin $B_2$ receptor was cloned by Hess et al. (Biochem. Biophys. Res. Comm., (1992), 184, 260–268). A human bradykinin $B_2$ receptor was expressed in CHO/K cells. Briefly, approximately 2×10$^6$ plaques from a human uterus λ gt10 cDNA library (Clontech Laboratories; Palo Alto, Calif.) were screened using a PCR fragment containing the coding region of the rat $B_2$ receptor. This probe was generated by random-primed synthesis in the presence of α[$^{32}$P]dATP. Duplicate filters were hybridized overnight at 42° C. in 1M NaCl, 50 mM Tris pH 7.5, 5X Denhardt's, 200 µg/ml salmon sperm DNA, 1% SDS, and 20% formamide. The filters were washed at 65° C. in 1X SSC and 1% SDS. Coincident positively hybridizing plaques were purified and rescreened with the same probe and stringency conditions. EcoR I fragments of positive clones were inserted into Bluescript/KS II+vector (Stratagene; La Jolla, Calif.) for sequence determination.

The nucleotide sequence of the cloned human $B_2$ receptors was determined using double-stranded DNA and the dideoxy chain termination method. Commercially available T3 and T7 oligonucleotides (USB; Cleveland, Ohio) and synthetic 21-met oligonucleotides (DNA/RNA Synthesizer; Applied Biosystems Inc.; Palo Alto, Calif.) from both the known rat sequence and the determined human sequence were used to identify the nucleotide sequence from the 5' untranslated end to the Bgl II site in the 3' untranslated end of the clone. The Hind III/Xba I fragment of one full-length clone, 126A, was inserted into pcDNA I neo vector (Invitrogen; San Diego, Calif.) for expression in mammalian cell lines.

CHO/K cells were plated in 2 ml of growth medium (Ham's F12 with 10% FBS) per 6 well plate and incubated at 37° C., 5% $CO_2$ until they were 60% confluent. For each well, 4, 12, and 16 µg of DNA was diluted in 100 µl Opti-MEM I reduced serum medium (Gibco/BRL; Gaithersburg, Md.). 12 µl of TransfectASE reagent (Gibco/BRL) was diluted in a separate aliquot of 100 µl Opti-MEM I. The DNA and TransfecASE solutions were combined, mixed gently, and incubated at 25° C. for 15 minutes. This solution was then diluted to 1 ml with Opti-MEM I. Each well was washed twice with Opti-MEM I and 1 ml of the DNA/TransfectAse complex was added to each well. After a 5 hour incubation at 37° C. and 5% $CO_2$, 1 ml of Ham's F12 with 20% FBS was added to each well and cells were incubated overnight. Media was replaced with growth medium and incubated for additional 24 hours.

Cells were harvested by trypsinization and replated in selection medium (Ham's F12, 10% FBS and 500 µg/ml Geneticin (Gibco/BRL). Media was replaced every 48 hours for 2 weeks. Any colonies remaining after selection were transferred to separate 10 cm dishes, grown to confluency and positive clones were determined by binding of $^3$H-NPC 17731, a bradykinin antagonist peptide described by Burch et at. (DuPont Biotech Update, (1992), 4, 127–140). Colonies expressing the receptor were put out at limiting dilution. Cells were expanded and positive clones were identified as above. A cell line designated H2O.2 was used to quantitate binding of the compounds of the invention to the human bradykinin $B_2$ receptor.

Radioligand Binding Assays

H2O.2 cells were grown to confluency in Ham's F12 media containing 10% FBS and 500 µg/ml Geneticin. Growth media was aspirated and the monolayer washed once with Dulbecco's PBS without $Ca^{++}$ and $Mg^{++}$. Cells were scraped in Dulbecco's PBS and centrifuged at 2000×g for 10 minutes. Pellets were resuspended in 25 mM TES, 1 mM 1,10-phenanthroline pH 6.8 buffer and homogenized using a Ploytron at setting 5 for 10 seconds. An aliquot was taken for a protein determination using a BioRad protein assay kit. Membranes were centrifuged at 48000×g for 10 minutes at 4° C. Pellets were resuspended in the TES buffer with 0.1% BSA and 0.014% bacitracin. 0.5 ml aliquots were frozen in liquid $N_2$ and stored at −80° C. for up to 2 weeks.

Membranes from $H_2O.2$ cells previously prepared were thawed at 37° C. and diluted in 25 mM TES, 1 µM 1,10-phenanthroline pH 6.8 containing BSA and bactiracin. For saturation binding assays, increasing concentrations of 3H-bradykinin or 3H-NPC 17731 were incubated with 16.5 µg of membrane protein in a total volume of 3 ml of the same buffer. Non-specific binding was determined with 1 µM bradykinin. The tubes were incubated 90 minutes at 25° C. and the assay was terminated by rapid vacuum filtration onto Whatman GF/B filters presoaked with 0.2% PEI for 3 hours followed by 2×3 ml aliquots of ice-cold 50 mM Tris, pH 7.4. Radioactivity was counted with a Beckman scintillation counter. The test results obtained are shown in Table I.

EXAMPLE 7

Determination of Bradykinin Antagonist Activity

The protocol was designed to identify compounds that possess antagonist activity at bradykinin receptors on intestinal (ileal longitudinal) smooth muscle.

Guinea pig intestine was removed and placed in a Petal dish containing Tyrodes solution and cut into 3–4 cm segments. The longitudinal muscle was separated from the underlying circular muscle using a cotton applicator (Paton and Zar, J. Physiol., (1968), 194:13). Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 ml tissue baths to increase the concentration of bradykinin in the bath step-by-step without washing out after each single dose. Higher concentrations were added only after the preceding contraction had reached a steady value. When the next concentration step does not cause a further increase in contraction, it was assumed that the maximum effect had been obtained and the tissue was washed to remove bradykinin and allowed to recover for 15 minutes. Antagonism of bradykinin responses in the presence of antagonist were determined by repeating the cumulative addition procedure for bradykinin after the tissue has been exposed to the antagonist for 5 minutes. Three or four different concentrations of antagonist are studied sequentially in the same preparations. Responses were expressed as a percentage of the maximum contraction elicited by bradykinin in the absence of antagonist. pA2 values were calculated by Schild analysis.

The invention being thus described, it will be obvious that the same may be varied in many ways. Such variations are not to be regarded as a departure from the spirit and scope of the invention and all such modifications are intended to be included within the scope of the following claims.

EXAMPLE 8

Determination of $B_1$ receptor antagonist activity

The ability of a pseudopeptide of the invention to antagonize $B_1$ receptor mediated inflammatory responses in vivo can be confirmed by testing the ability of the pseudopeptide to inhibit des $Arg^9$-bradykinin induced hypotension in rabbits pretreated with lipopolysaccharide. It is known that, in the presence of inflammation-inducing substances, including lipopolysaccharide and interleukin 1, $B_1$ receptors are upregulated and respond to des $Arg^9$-bradykinin to produce inflammatory responses, including hypertension.

Male New Zealand white rabbits (1.5–2.0 kg) are pretreated with a freshly made solution of LPS (10 µg/100 µl) 5 hr prior to anesthetizing with sodium phenobarbital i.v. The left carotide artery is cannulated for recoding mean arterial blood pressure and the left jugular vein for des $Arg^9$-bradykinin (1 µg/kg) and the pseudopeptide to be tested. Animals are pulsed with a bolus of des $Arg^9$-bradykinin (3x) at 5 min intervals to produce a basal hypotensive response. Test pseudopeptide is then administered as a bolus prior to des $Arg^9$-bradykinin and its ability to antagonize the $B_1$-mediated hypotensive response is determined as % inhibition.

TABLE I

| NPC No. Compound | | $K_i$ (nM) Human 17731 | Guinea Pig |
|---|---|---|---|
| 18424 |  H-D-Arg—Arg—Pro—N ... Phe—Ser-D-Hype(trans-thiophenyl)-Oic—Arg—OH | 15 | 174 |
| 18465 | 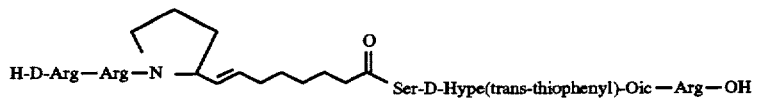 H-D-Arg—Arg—N ... Ser-D-Hype(trans-thiophenyl)-Oic—Arg—OH | | 2123 |
| 18466 | 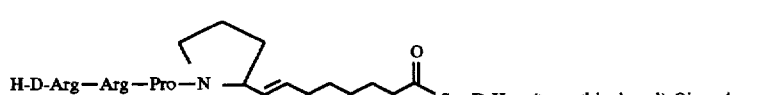 H-D-Arg—Arg—Pro—N ... Ser-D-Hype(trans-thiophenyl)-Oic—Arg—OH | | 1896 |
| 18467 | 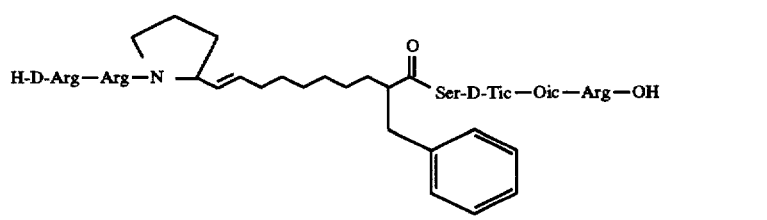 H-D-Arg—Arg—N ... Ser-D-Tic—Oic—Arg—OH | | 400 |

TABLE I-continued

| NPC No. Compound | K₁ (nM) Human 17731 | Guinea Pig |
|---|---|---|
| 18484  H-D-Arg—Arg—Pro—Hyp—N(H)—CH=CH—CH(CH₂Ph)—C(O)—Ser-D-Tic—Oic—Arg—OH | | 358 |
| 18608  H-D-Arg—Arg—N(2-pyrrolidinyl)—CH=CH—CH₂CH₂—CH(CH₂Ph)—C(O)—Ser-D-Tic—Oic—Arg—OH | | 21 |
| H-D-Arg—Arg—NH—(o-C₆H₄)—CH=CH—CH₂—C(O)—Phe—Ser-D-Tic—Oic—Arg—OH | | 1267 ± 173 |
| H-D-Arg—Arg—NH—(o-C₆H₄)—CH=CH—CH₂—C(O)—N-benzyl-Gly—Ser-D-Tic—Oic—Arg—OH | | 28 |

We claim:

1. A pseudopeptide which has an affinity for the bradykinin $B_1$ receptor having the formula:

A—B—C—D—E—F—G—H—I—K wherein

A is selected from the group consisting of the L- and D-isomers of Arg and Lys;

B is selected from the group consisting of the L- and D-isomers of Arg and Lys;

C is a direct bond or is selected from the group consisting of Pro, 4Hyp and Oic;

D is selected from the group consisting of 2-pyrrolidinyl, Pro, 4Hyp and Oic;

E has the following formula:

$$-X-(CH_2)_m-Z_1-(CH_2)_n-Z_2-(CH_2)_o-\underset{\underset{Y}{|}}{C}H-\underset{\underset{O}{||}}{C}-$$

wherein

X is selected from the group consisting of a direct bond and an imino (—NH—) group;

$Z_1$ is a $C_2$ to $C_{18}$ monoolefin;

$Z_2$ is a direct bond;

Y is selected from the group consisting of hydrogen, hydroxymethyl, $C_1$ to $C_6$ alkyl, benzyl, thiophenylmethyl and furanylmethyl;

m, n and o are independently 0 to 6;

F is a direct bond or is selected from the group consisting of Phe and N-benzyl-Gly;

G is selected from the group consisting of Ser, Thr, Gly and Val;

H is selected from the group consisting of a D-Phe, D-Tic and a D-trans-Hype in which an aryl group, if present, is selected from the group consisting of benzyl, phenyl and naphthyl;

I is selected from the group consisting of Oic, Aoc, Tic, Phe, and a Hype in which an aryl group, if present, is selected from the group consisting of benzyl, phenyl and naphthyl;

K is selected from the group consisting of a hydroxyl moiety, an amino moiety and an alkoxy moiety;

or a pharmaceutically acceptable salt thereof.

2. A method of treating chronic inflammation in a mammal in need of such treatment which method comprises administering to said mammal a compound of claim 1 in an amount effective to alleviate said chronic inflammation.

* * * * *